United States Patent [19]

Goda et al.

[11] Patent Number: 4,902,783

[45] Date of Patent: Feb. 20, 1990

[54] METHOD FOR PURIFYING A GENE-EXPRESSION PRODUCT PRODUCED BY RECOMBINANT DNA TECHNIQUE

[75] Inventors: Hideo Goda; Toshiyuki Akiyama; Akihisa Takamizawa; Iwao Yoshida; Takeo Konobe, all of Kanonzi; Keisuke Takaku, Suita, all of Japan

[73] Assignee: The Research Foundation for Microbial Diseases of Osaka University, Osaka, Japan

[21] Appl. No.: 61,503

[22] Filed: Jun. 15, 1987

[30] Foreign Application Priority Data

Jun. 18, 1986 [JP] Japan ................... 61-143413

[51] Int. Cl.⁴ .................... C07K 3/18; C07K 3/12; C07K 3/28
[52] U.S. Cl. .................... 530/415; 530/412; 530/427; 435/69.1
[58] Field of Search ............ 530/415, 412, 427; 435/803, 815, 68; 210/660; 424/89

[56] References Cited

U.S. PATENT DOCUMENTS

| 3,636,191 | 1/1972 | Blumberg | 530/806 |
|---|---|---|---|
| 3,951,937 | 4/1976 | Vneck | 435/803 |
| 4,503,035 | 3/1985 | Pestka et al. | 424/85 |
| 4,505,893 | 3/1985 | Mori et al. | 424/94 |
| 4,508,709 | 4/1985 | Amphlett et al. | 424/101 |
| 4,508,833 | 4/1985 | Sonneborn et al. | 436/543 |
| 4,514,506 | 4/1985 | Braatz et al. | 436/518 |
| 4,525,459 | 6/1985 | Fletcher | 436/544 |
| 4,552,758 | 11/1986 | Murphy et al. | 424/89 |
| 4,554,157 | 11/1986 | Skelly et al. | 424/89 |
| 4,565,697 | 1/1986 | Ohmura et al. | 424/89 |
| 4,578,269 | 3/1986 | Morein | 424/88 |
| 4,649,192 | 3/1987 | VanWijnendoele et al. | 530/415 |

FOREIGN PATENT DOCUMENTS 0140386 5/1985 European Pat. Off. .
WO/05631 1/1985 World Int. Prop. O. .

OTHER PUBLICATIONS

Hassler, John W., *Purification with Activated Carbon*, N.Y., N.Y., Chemical Publishing Co., Inc., 1974, pp. 102–106.
Osterman, L. A., *Methods of Protein and Nucleic Acid Research*, vol. 1, N.Y., Springer—Verlag, 1984, pp. 241, 248, 249, 284, 285.
Methods in Microbiology, vol. 5B, 425–454, (1971), Academic Press, England.
Proc. Natl. Acad. Sci., 76, 5601–5605, (1979).
Nucleic Acids Research, 11, 2745–2763, (1983).

Primary Examiner—Margaret Moskowitz
Assistant Examiner—Keith C. Furman
Attorney, Agent, or Firm—Armstrong, Nikaido, Marmelstein, Kubovcik & Murray

[57] ABSTRACT

There is disclosed a method for purifying a gene-expression product produced by recombinant DNA technique which comprises a specific sequence of steps including adsorption treatment with silica gel, adsorption treatment with activated carbon, at least twice density gradient centrifugation and at least twice equilibrium density gradient centrifugation. The method of the present invention is very effective to remove allergen from gene-expression products contaminated therewith, enabling highly purified gene-expression products to be produced on a large scale.

5 Claims, No Drawings

METHOD FOR PURIFYING A GENE-EXPRESSION PRODUCT PRODUCED BY RECOMBINANT DNA TECHNIQUE

BACKGROUND OF THE INVENTION

1. Field of The Invention

The present invention relates to a method for purifying a gene-expression product produced by recombinant DNA technique. More particularly, the present invention is concerned with a method for purifying useful substances which are obtained from a culture of transformants prepared by recombinant DNA technique, by which allergen derived from the transformants and inevitably contained in the useful substances is effectively removed. By the method of the present invention, useful substances produced biologically can be efficiently purified to such an extent that no allergen is detected by any customary analysis. The method of the present invention is especially useful for the purification of active ingredients for drugs and quasi-drugs to be directly administered or applied to a human body. For example, the present method is extremely useful in the preparation of vaccine antigens, enzymes for pharmaceutical use, enzymes for toothpaste and toothpowder, proteins for cosmetics, etc.

2. Discussion Of Related Art

When a living body is antigenically stimulated by inoculation or inhalation of an antigen, the living body produces an antibody which specifically reacts with the antigen. Thereafter, if the same kind of antigen as the above-mentioned antigen enters the living body, an antigen-antibody reaction occurs in the living body, causing the antigen to be destroyed as a foreign matter. This is a protection mechanism against infections and called an immunity phenomenon. In some cases, however, upon entrance of an antigen, there occurs an abnormal or hypersensitive reaction, such as local inflammation or a sudden shock which is quite different from the immunity phenomenon. This abnormal reaction is called an allergic reaction. At present, the allergic reaction is classified into four types, i.e. Types I, II, III and IV, according to the manifestation of the allergic reaction and the condition of the patient. Among the four types, Type I is well known as a major allergic reaction and is called immediate-type allergy or anaphilaxis. In the cases of human bodies, it is said that Type I allergy is generally caused by immunogloblin E (IgE) antibody. Illustratively stated, if a human body is stimulated by an allergen as an antigen, IgE antibody against the allergen is produced in the body and carried thereby. Thereafter, if the same kind of allergen as mentioned above enters the body, an antigen-antibody reaction occurs between the allergen and the IgE antibody, thereby causing an allergic reaction. Substances which are known as allergen or sources of allergen are, for example, pollens, insects, skin fragments, mold, substances derived from microorganisms, foods, drugs, chemical, etc. In general, the amount of IgE antibody carried by human bodies, which is reactive to such substances, can be measured by a passive cutaneous anaphylaxis (PCA) reaction test.

Contamination of vaccine injections and the like, which are administered directly to human bodies, with allergen as an impurity greatly impairs medicines which must be safe. However, in the preparation of biological medicines such as a vaccine, there are still many requirements and problems to be studied concerning activity, safety and homogeny, and, therefore, the investigations currently conducted in the field has not yet been extended to development of a high-order purification technique giving priority especially to the removal of allergen. [See, for example, Methods in Microbiology, vol. 5B, pp. 425-454 (1971), Academic Press, England; Proc. Natl. Acad. Sci., 76, 5601-5605 (1979); and Nucleic Acids Research, 11, 2745-2763 (1983).]

Recently, there has been made an attempt to reduce the IgE antibody inducing ability of allergen by modifying allergen with polyethylene glycol, pullulan, dextran, a polyamine, a fatty acid, urea, glutaraldehyde, formalin, etc. However, this study is still at the basic stage.

Incidentally, the rapid development of the genetic engineering in recent years has made it possible to prepare transformants of microorganisms and somatic cells and to produce various useful substances from cultures of such transformants. On the other hand, such useful substances are likely to be contaminated with allergen derived from the transformants. However, in the field of genetic engineering also, importance is not yet placed on the high-order purification for removing allergen from gene-expression products contaminated therewith. Although affinity chromatography in which a monoclonal antibody is used, large-scale electrophoresis, etc. have been developed for purifying gene-expression products, they are not so effective for removing allergen derived from the transformants. Further, the purification by affinity chromatography has drawbacks that since extremely low pH values are employed for eluting the adsorbed product, the proteinous product to be purified is liable to be denatured, resulting in low immunogenicity of the product and that when the desired product adsorbed in the column is eluted, the product is necessarily contaminated by the antibody, so that an additional purification for removing the antibody is needed. On the other hand, in the purification by electrophoresis, there are also various disadvantages, such as restriction of employable medium, susceptibility of purification degree to the conditions of the operation, so that electrophoresis is not suited for a large-scale purification.

Besides the above-mentioned purification methods, the purification by gel filtration and ion exchange column chromatography have been proposed, but they are also defective. For example, in the case where a crude product containing the surface antigen of hepatitis B virus (HBs antigen) is purified by gel filtration, the yield of HBs antigen is very low, for example as low as 5 to 20%, and the HBs antigen is liable to be inactivated in the column due to the low concentration of HBs antigen. In the case where a crude product containing HBs antigen is purified by ion exchange column chromatography, the purity of the product after the purification is insufficiently low.

In connection with the above-mentioned customary purification methods, reference can be made to the following:
International Patent Application (PCT) Publication No. WO85/05631
European Patent Application Publication No. 0 140 386
U.S. Pat. No. 4,503,035
U.S. Pat. No. 4,505,893
U.S. Pat. No. 4,508,709
U.S. Pat. No. 4,508,833
U.S. Pat. No. 4,514,506
U.S. Pat. No. 4,525,459

U.S. Pat. No. 4,552,758
U.S. Pat. No. 4,554,157
U.S. Pat. No. 4,565,697
U.S. Pat. No. 4,578,269

Accordingly, in the field of the genetic engineering including the biological production of medicines, it is of urgent necessity to establish a high-order purification technique for removing allergen derived from transformants and contained in gene-expression products.

SUMMARY OF THE INVENTION

In view of the current situation as described above, the present inventors have made intensive and extensive studies with a view to the developing of an effective method for removing allergen from gene-expression products contaminated therewith. As a result, they have unexpectedly found that a purification method comprising a sequence of steps of adsorption treatment with silica gel, adsorption treatment with activated carbon, at least two density gradient centrifugation and at least two equilibrium density gradient centrifugation is extremely effective for removing allergen from gene-expression products produced by recombinant DNA technique. By such a novel purification method, there can be obtained a highly purified gene-expression product from which allergen derived from the transformant is removed to such an extent that no allergen is detected by PCA reaction test. Further, using the novel purification method, a large-scale high order purification can be effected stably. Based on the novel finding, the present invention has been completed.

Accordingly, it is an object of the present invention to provide a method for purifying gene-expression products, which is extremely effective for completely removing allergen derived from the transformants and contained in the gene-expression products.

DETAILED DESCRIPTION OF THE INVENTION

According to the present invention, there is provided a method for purifying a gene-expression product produced by recombinant DNA technique which comprises the steps of:

(a) subjecting a crude aqueous solution containing a gene-expression product which solution is obtained from a culture of a transformant prepared by recombinant DNA technique to adsorption treatment with silica gel, thereby causing the gene-expression product to be adsorbed on said silica gel, (b) eluting said gene-expression product adsorbed on said silica gel to obtain an eluate containing the gene-expression product, (c) subjecting said eluate to adsorption treatment with activated carbon, thereby causing impurities in said eluate to be adsorbed on said activated carbon, followed by recovery of the resulting eluate, (d) subjecting said resulting eluate treated in step (c) to density gradient centrifugation at least two times to obtain a preliminary fraction containing the gene-expression product, and (e) subjecting said preliminary fraction obtained in step (d) to equilibrium density gradient centrifugation at least two times to obtain a final fraction containing the gene-expression product.

By the method of the present invention, not only allergen derived from transformants but also allergen derived from naturally existing microrganisms and somatic cells can be efficiently removed. Further, since the purification of a gene-expression product according to the method of the present invention can be performed under moderate pH conditions in all the steps involved therein, the gene-expression product does not undergo denaturation and, hence, a high quality of the gene-expression product can be attained.

The gene-expression products which can be purified by the method of the present invention means a substance produced directly by gene-expression in a transformant. As the primary products, there may be mentioned, for example, proteinous substances such as virus antigens including a hepatitis B virus and a flavivirus antigens, enzymes, hormones, interferon and other proteinous physiologically active substances.

A crude aqueous solution containing a gene-expression product which is to be subjected to adsorption treatment with silica gel can be prepared as follows. In the case where the gene-expression product is excreted from the cells, the cells are removed from the culture by a customary method and then the resulting culture is used as the crude aqueous solution containing the gene-expression product. In the case where the gene-expression product is not excreted from the cells, the cells are collected from the culture and disrupted, followed by removal of the disrupted cell residues to prepare a crude aqueous solution containing the gene-expression product. For the disruption of cells, various known treatments may be employed such as lysis with an enzyme, disruption treatment utilizing osmotic pressure, ultrasonic treatment, and treatment with various types of homogenizers. Of these, treatment with a pressure homogenizer is preferred.

The thus prepared crude aqueous solution containing a gene-expression product is subjected to adsorption treatment with silica gel. This treatment may be effected, for example, by adding silica gel to the crude aqueous solution, followed by stirring to cause the gene-expression product to be adsorbed on the silica gel. Then, the supernatant liquid is removed, and the silica gel is washed with, for example, a buffer such as a carbonate buffer.

The silica gel to be used in this step is not specifically limited, and there may be used a silica gel generally employed as an adsorbent for example, a commercially available silica gel powder for the purification by column chromatography. The amount of the silica gel is generally in the range of from about 0.1 to 10 w/v % based on the crude aqueous solution containing a gene-expression product. The stirring is generally effected at 10° to 30° C. for 10 to 100 minutes.

Subsequently, the gene-expression product adsorbed on the silica gel is eluted. The elution may be effected, for example, by adding an appropriate eluent to the silica gel, stirring the mixture, subjecting the mixture to centrifugation or the like, and removing the silica gel to obtain an eluate. The stirring is generally effected at 10° to 30° C. for 10 to 100 minutes.

The above-explained step of adsorption treatment with silica gel and step of elution may also be effected by the customary column chromatography. The adsorption of the gene-expression product on the silica gel and the desorption, i.e., elution of the product can be efficiently effected by appropriately adjusting the pH value and ionic strength of the crude aqueous solution and eluent.

Next, the eluate obtained in the above step is subjected to adsorption treatment with activated carbon to cause impurities to be adsorbed on the activated carbon.

Before being subjected to the adsorption treatment with activated carbon, the eluate may be subjected to ultrafiltration to concentrate the eluate, followed by addition of a fresh buffer.

The adsorption treatment with activated carbon may be effected by adding activated carbon to the eluate, followed by stirring generally at 10° to 30° C. for 5 to 30 minutes. By this treatment, only the impurities are adsorbed on the activated carbon while leaving the gene-expression product unadsorbed. After the stirring, the activated carbon is separation-removed by centrifugation or the like to obtain a supernatant. The resulting eluate, i.e. the supernatant obtained, may be concentrated by a customary method for the next step of density gradient centrifugation as will be mentioned later.

The active carbon to be used in this step is not specifically limited, and commercially available activated carbons such as powdery ones may be used. The amount of the active carbon is generally in the range of from about 0.1 to 10 w/v % based on the eluate.

The above-explained step of adsorption treatment with activated carbon may also be effected by customary column chromatography.

Before being subjected to density gradient centrifugation, the resulting eluate may be subjected to acid treatment to further remove impurities. Illustratively stated, for example, an aqueous hydrochloric acid solution is added to the resulting eluate to lower the pH of the eluate to about 4.0 to 6.5, causing impurities to be precipitated, and the precipitate is separation-removed by centrifugation or the like. After the acid treatment, the pH of the eluate is adjusted to 7.0 to 9.0 with an alkaline solution such as an aqueous sodium hydroxide solution.

According to need, the resulting eluate obtained by the adsorption treatment with activated carbon may be subjected to additional adsorption-desorption treatment with alumina, Celite ® or the like.

The resulting eluate treated with activated carbon is then subjected to density gradient centrifugation at least two times. The density gradient centrifugation may be effected by a customary known method. The density gradient of the carrier medium in a centrifugal column may be such that the density of the carrier medium increases linearly or discontinuously from the uppermost portion to the lowermost portion of the carrier medium. The discontinuous stepwise density change may be obtained by superimposing a plurality of solutions having different densities to form a density gradient.

As solutes which may be used for obtaining the density gradient, there may be mentioned customarily employed substances including sucrose, deuterium oxide, diodone, Ficoll ®, potassium bromide, polyvinyl pyrrolidone, cesium chloride, etc. Of them, sucrose is preferred from the viewpoints of the stability of the density gradient during the centrifugation, economics, safety and facility in use.

The respective density gradient centrifugation treatments, which are conducted at least two times, may be effected using centrifugal columns having the same density gradient, or alternatively, using centrifugal columns having different density gradients. In the case where the respective density gradient centrifugation treatments are effected using centrifugal columns having different density gradients, the density gradient is changed such that the density range becomes small as the treatment is repeated.

The density gradient of the column may vary depending on the kind of the gene-expression product and the kind of the contaminatants. Generally, however, for the first density gradient centrifugation, the lowest solute concentration in the carrier medium may be not lower than 5 w/w % and the highest solute concentration in the carrier medium may be not higher than 60 w/w %, and the difference between the lowest and highest solute concentrations in the carrier medium may be from 10 to 55 w/w %. For the second density gradient centrifugation and any subsequent density gradient centrifugation, the lowest solute concentration in the carrier medium may be not lower than 5 w/w % and the highest solute concentration in the carrier medium may be not higher than 50 w/w %, and the difference between the lowest and highest solute concentrations in the carrier medium may be from 5 to 45 w/w %. The density gradient centrifugation may generally be effected at about 20,000 to 40,000 rpm (29,000 to 118,000×g) for about 2 to 30 hours.

After the first density gradient centrifugation treatment, a fraction containing the desired gene-expression product is collected. The fraction thus obtained may be subjected to concentration treatment, dialysis and/or filtration according to known methods, before being subjected to the second density gradient centrifugation treatment.

The fraction obtained by at least two density gradient centrifugations is then subjected to equilibrium density gradient centrifugation at least two times. The equilibrium density gradient centrifugation may be effected by a usual method. The carrier medium in the centrifugal column to be used in this step may have a uniform solute concentration, or may have a discontinuously varied solute concentration which is formed by superimposing, for example two or three solutions having different solute concentrations.

As solutes which may be used for preparing the carrier medium, there may be mentioned the same kinds of substances as described above with respect to the density gradient centrifugation. However, from the viewpoints of ease in formation of density gradient during the centrifugation, economics and ease of disposal as industrial wastes, potassium bromide is preferred.

The respective equilibrium density gradient centrifugation treatments, which are conducted at least two times, may be effected using the centrifugal columns having the same density, or using centrifugal columns having different densities. In the case where the equilibrium density gradient centrifugation treatments are effected using centrifugal columns having different densities, the density is changed such that it becomes low as the treatment is repeated.

The density of the carrier medium in the column may vary depending on the kind of the gene-expression product and the kind of the contaminants. Generally, however, for the first equilibrium density gradient centrifugation, the solute concentration of the carrier medium may be from 10 to 40 w/w %. For the second equilibrium density gradient centrifugation and any subsequent equilibrium density gradient centrifugation, the solute concentration of the carrier medium may be from 20 to 40 w/w %. The centrifugation may generally be effected at about 30,000 to 60,000 rpm (45,000 to 180,000×g) for about 30 to 80 hours.

After the first equilibrium density gradient centrifugation treatment, a fraction containing the desired gene-expression produced is collected. The fraction thus obtained may be subjected to concentration treatment, dialysis and/or ultrafiltration according to known methods, before being subjected to the second equilibrium density gradient centrifugation treatment.

Thus, a highly purified gene-expression product can be obtained.

As explained hereinbefore, the method of the present invention consists in a specific combination of purification techniques. Due to the specific combination of purification techniques, the allergen contained in gene-expression product which is derived from the transformant can be effectively and almost completely removed and, hence, a highly purified gene-expression product can be obtained. Further, a gene-expression product can be purified under moderate pH conditions in all the steps of the present invention, so that the purified product has a high quality as different from the product obtained by the customary affinity chromatography which requires extremely low pH conditions for its elution step.

In practicing the method of the present invention, the selection of physicochemical factors such as temperature, pressure, pH, concentration and ionic strength, the selection of purification reagents such as an adsorbent, an eluent and a dispersing agent, and the selection of purification instruments and apparatus such as a centrifuge, a filter, an instrument for electrophoresis and a homogenizer can be appropriately made according to the kind of the desired gene-expression product, the kind of contaminants and the like.

DETAILED DESCRIPTION OF THE PREFERRED EMBODIMENT

This invention will now be described in detail with reference to the following Examples, Referential Examples and Comparative Example but they should not be construed to be limiting the scope of the present invention. In Example 1, the detection and measurement of HBs antigen after each purification step were carried out in substantially the same manner as in Referential Example 2

REFERENTIAL EXAMPLE 1

From *E. coli* $\chi$1776/pM1B11 (deposited with the Fermentation Research Institute under the accession number FERM BP-1081) containing a plasmid pM1B11 carrying DNA coding for the surface antigen of hepatitis B virus (hereinafter, referred to as HBs antigen), the plasmid pM1B11 was extracted with phenol. From the plasmid pM1B11, a DNA fragment containing a DNA coding for HBs antigen was taken out by means of restriction enzymes XhoI and BamHI. On the other hand, plasmid pHO5 obtained according to Kenji Arima et al., Nucleic Acid Research, 11, 1657-1672 (1983) was digested with restriction enzymes BamHI and SalI to obtain a DNA fragment of about 0.6 kb containing a PHO5 promoter. To the downstream of the thus obtained DNA containing a promoter of PHO5 gene which codes for repressible acid phosphatase of yeast, the above-obtained DNA fragment containing a DNA coding for HBs antigen was linked by means of T4 DNA ligase, thereby to obtain a DNA fragment. The DNA fragment was inserted at the BamHI site of a plasmid pBR325, followed by cloning to obtain a plasmid which is capable of expressing the gene coding for HBs antigen. Using the plasmid thus obtained, a yeast *Saccharomyces cerevisiae* SHY4 (ATCC No. 44772) was transformed, thereby obtaining a transformant yeast.

EXAMPLE 1

Step 1

The transformant yeast obtained in Referential Example 1 was cultured in complete-synthetic Burkholder medium [a medium containing 20 μg/ml each of uracil, L-tryptophan and L-histidine; Burkholder P. R., et al., Am. J. Botany 30, 206(1943)]containing 1.5 g/l of potassium dihydrogenphosphate at 30° C. for 24 hours. The culture obtained was subjected to centrifugation at 12,000×g for 10 minutes, and the cells were collected. 50 g of the thus obtained wet cells were washed in 500 ml of a 1/10M phosphate buffer (pH 9.0), followed by centrifugation under the same conditions as the above to recover the cells. The above-mentioned washing and recovery of the cells were repeated again.

Step 2

The cells obtained in Step 1 were suspended in 500 ml of a 1/100M phosphate buffer (pH 9.0). The suspension was treated with a pressure homogenizer (manufactured and sold by Gaulin Co., U.S.A.) at 8,000 to 10,000 psi to disrupt the cells. Then, the suspension thus treated was subjected to centrifugation at 12,000×g for 20 minutes to separate the suspension into a supernatant and a pellet, and the supernatant was collected. The supernatant thus obtained as a crude extract containing an HBs antigen was subjected to the subsequent step.

Step 3

To the crude extract obtained in Step 2 was added sodium chloride so that the final concentration of sodium chloride became 0.2M, followed by mixing. To the resulting mixture was added silica gel so that the content of the silica gel became 2 w/v %. Subsequently, the mixture was stirred at room temperature for 30 minutes, thereby causing the HBs antigen to be adsorbed on the silica gel. The silica gel adsorbing the HBs antigen was collected through centrifugation at 5,000×g for 10 minutes. To the silica gel thus collected was added 250 ml of carbonate buffer (pH 10), followed by stirring at room temperature for 40 minutes to elute the HBs antigen from the silica gel. Then, the resulting mixture containing an eluate and the silica gel was subjected to centrifugation at 5,000×g for 10 minutes to separate the mixture into the eluate and the silica gel, and the silica gel was removed and the eluate was collected.

Step 4

To the eluate obtained in Step 3 was added, active carbon so that the content of the activated carbon became 1 w/v %, followed by stirring at room temperature for 10 minutes. The mixture was then subjected to centrifugation at 10,000×g for 10 minutes to separate into the activated carbon and a supernatant, and the activated carbon was removed and the supernatant was collected. To the supernatant was dropwise added 0.02N hydrochloric acid to adjust the pH of the supernatant to 6.0, and the resulting mixture was stirred at 10° C. for 30 minutes. As a result, an acid precipitate was formed. The precipitate was removed by centrifugation at 10,000×g for 10 minutes and the supernatant was collected. To the supernatant was drop-wise added a 0.02N aqueous sodium hydroxide solution to adjust the pH of the supernatant to 8.0, and the supernatant was then concentrated by means of an ultrafiltrator (produced and sold by Millipore Co., U.S.A.), to obtain 25 ml of a concentrate containing an HBs antigen.

Step 5

The concentrate obtained in Step 4 was subjected to density gradient centrifugation at 30,000 rpm (45,000×g) for 18 hours, and a fraction containing HBs antigen was collected. The carrier medium used was a sucrose density gradient medium having a lowest sucrose concentration of 20 w/w % and a highest sucrose concentration of 30 w/w %. The centrifuge used was zonal rotor RPZ-35T manufactured and sold by Hitachi Koki Co., Ltd., Japan. The fraction thus obtained was dialyzed against 1/200M phosphate buffer (pH 9.0) for 24 hours to remove the sucrose. The above-mentioned operation was repeated again.

Step 6

10 ml of the HBs antigen fraction obtained in Step 5 was admixed with 40 ml of 1/200M phosphate buffer containing 40 w/w % potassium bromide. The resulting mixture was subjected to equilibrium density gradient centrifugation at 45,000 rpm (125,000×g) for 48 hours, and a fraction containing HBs antigen was collected. The centrifuge used was rotor RP-50T-2 manufactured and sold by Hitachi Koki Co., Ltd., Japan. Then, the collected fraction was dialyzed against 1/200M phosphate buffer (pH 9.0) for 24 hours to remove the potassium bromide. The above-mentioned operation was repeated again to obtain a highly purified HBs antigen product.

Step 7

The purity of the HBs antigen obtained in Step 6 of Example 1 was determined using an SDS-polyacrylamide gel electrophoresis kit (SDS-PAGE kit) manufactured and sold by Daiichi Kagaku Co., Ltd., Japan. That is, the purified HBs antigen product was subjected to serial doubling dilution with a buffer containing 20 w/w % glycerol, 0.1M Tris (pH 6.8), 2 w/w % SDS, 0.004 w/w % Bromophenol Blue and 10 w/w % 2-mercaptoethanol to prepare HBs antigen samples having respective dilutions. Each of the samples was applied to an SDS-polyacrylamide gel and subjected to electrophoresis, followed by silver-staining. Then, the purity of the HBs antigen was calculated from a ratio of a degree of dilution of the purified HBs antigen product beyond which degree of dilution the impurities were no longer silver-stained to a degree of dilution beyond which the HBs antigen was no longer silver-stained. As a result, it was found that the purity of the HBs antigen was 99.5% or more.

Step 8

Mouse anti-HBs antigen serums were obtained from female BALB/c mice (5-week age) immunized with the purified HBs antigen obtained in Step 6 of Example 1. On the other hand, mouse anti-yeast serums were obtained from female BALB/c mice (5-week age) immunized with a crude extract of yeast cells which was obtained in substantially the same manner as in Step 2 of Example 1. The doses of the purified HBs antigen and the crude yeast extract used for immunization were varied as indicated in Table 1.

With respect to each of the serums thus obtained, the content of IgE antibody against yeast was evaluated according to the passive cutaneous anaphylaxis (PCA) reaction test. That is, each of the serums was subjected to serial doubling dilution with a physiological saline, and separately inoculated subcutaneously upon respective female SW rats into the back skin in an amount of 0.1 ml. 24 Hours after the inoculation, 1 ml of a physiological saline containing 0.5 w/v % Evans' Blue and 1 mg, in terms of the amount of proteinous nitrogen, of a crude extract of yeast cells obtained in substantially the same manner as in Step 2 of Example 1 was injected to each of the rats through its tail vein. 30 Minutes after the injection, each rat was observed for blue puncta at the injection site. The appearance of blue puncta shows the presence of IgE antibody in the rat, and the non-appearance shows the absence of IgE antibody. The results are shown in Table 1, in which the PCA titer indicates the minimum dilution (times) of the serum at which blue puncta appeared. It is apparent from the results that the allergen derived from the yeast cells were satisfactorily removed from the HBs antigen obtained in Step 6 of Example 1.

TABLE 1

| Immunogen | Dose of purified HBs antigen product (μg protein) | Dose of crude yeast extract (μg protein) | PCA titer | IgE antibody |
|---|---|---|---|---|
| Mouse anti-yeast serum | | 4.0 | >40 | presence |
| | | 1.0 | 40 | presence |
| | | 0.25 | 10 | presence |
| | | 0.0625 | 5 | presence |
| | | 0.016 | <5 | absence |
| Mouse anti-HBs antigen serum | 8.0 | | <5 | absence |
| | 4.0 | | <5 | absence |
| | 2.0 | | <5 | absence |
| | 1.0 | | <5 | absence |
| | 0.5 | | <5 | absence |

EXAMPLE 2

From E. coli JM83/pS22 (deposited with the Fermentation Research Institute under the accession number FERM BP-1047) containing a plasmid pS22 carrying a DNA coding for the Japanese encephalitis virus V3 antigen, the plasmid pS22 was extracted with phenol. Subsequently, the MluI site of the plasmid pS22 was cleaved by means of a restriction enzyme MluI to obtain a linear plasmid having both ends formed by MluI cleavage. Both the ends of the linear plasmid were converted to blunt ends using T4 DNA polymerase. To the resulting blunt ends, XhoI linkers were ligated, followed by annealing. Thus, the MluI site of the plasmid was converted to an XhoI site. Thereafter, Universal terminator (manufactured and sold by Pharmacia Fine Chemicals Co., Sweden) was ligated to the plasmid at its SphI site. The resulting plasmid was designated plasmid pS22XS. From the plasmid pS22XS, a DNA fragment containing a DNA coding for Japanese encephalitis virus V3 antigen was taken out by means of restriction enzymens XhoI and SalI. In substantially the same manner as in Referential Example 1, the DNA fragment thus taken out was linked to the downstream of a DNA containing a promotor of PHO5 gene which codes for respressible acid phosphatase of yeast, and the DNA fragment obtained was inserted at the XhoI site of a plasmid YEp13 (ATCC No. 37115) to obtain a plasmid which is capable of expressing the gene coding for Japanese encephalitis virus V3 antigen. Using the plasmid thus obtained, a yeast Saccharomyces cerevisiae SHY4

(ATCC No. 44772) was transformed, thereby obtaining a transformant yeast.

The transformant yeast thus obtained was cultured and treated in substantially the same manners as in Step 1 and 2 of Example 1, thereby to obtain a crude extract containing a Japanese encephalitis virus V3 antigen. Using the crude extract, substantially the same procedures as in Steps 3 to 6 of Example 1 were repeated to obtain a highly purified Japanese encephalitis virus V3 antigen product. The purity of the V3 antigen was determined in substantially the same manner as in Step 7 of Example 1, and it was found to be 99.5 % or more. This showed that the allergens derived from the yeast cells were satisfactorily removed.

EXAMPLE 3

From the mutanase-producing strain SK-01 (deposited with the Fermentation Research Institute under the accession number FERM BP-9) which belongs to the genus Psuedomonas, a DNA was extracted according to the method described in "Experiment With Gene Fusion," pp. 137-139, Cold Spring Harbor Laboratory, USA (1984). To the thus obtained DNA extract was added a restriction enzyme EcoRI to partially digest the DNA. Thus, there was obtained a DNA fragment. The DNA fragment was ligated to the commercially available expression vector pYEJ001 plasmid [The Molecular Biology Catalog, p67, Pharmacia P-1, Biochemicals Co. (1985)]. Using the plasmid thus obtained, cells of *E. coli* K12 strain HB101 (ATCC No. 35673) was transformed to obtain transformants. From the transformants, those which are sensitive to chloramphenicol were selected and isolated. Subsequently, from the transformants sensitive to chloramphenicol, a transformant which produced mutanase was selected and isolated. The transformant thus obtained was designated *E. coli* K12HB10/pYEJM01. Also, the plasmid contained in the transformant was designated pYEJM01. This transformant was cultured and treated in substantially the same manners as in Steps 1 and 2 of Example 1, thereby to obtain a crude extract containing mutanase. Using the crude extract, substantially the same procedures as in Steps 3 to 6 of Example 1 were repeated to obtain a highly purified mutanase product. The purity of the mutanase was determined in substantially the same manner as in Step 7 of Example 1, and it was found to be 99.5% or more. This showed that the allergens derived from the *E. coli* were satisfactorily removed.

EXAMPLE 4

From the mutanase-producing transformant obtained in Example 3, a plasmid pYEJM01 was extracted with phenol. Then, from the plasmid pYEJM01, a DNA fragment containing a DNA coding for mutanase was taken out by means of restriction enzyme EcoRI. On the other hand, a plasmid pPL608 (ATCC No. 37108) as an expression vector was cleaved by means of a restriction enzyme HindIII, and was ligated to the above-obtained DNA fragment containing a gene coding for mutanase by means of T4 DNA ligase to obtain a plasmid. Using the plasmid thus obtained, cells of *Bacillus subtilis* BR151 (ATCC No. 33677) were transformed to obtain transformants. From the transformants, a transformant which produced mutanase was selected and isolated. The transformant thus obtained was designated *Bacillus subtilis* BR151/pPLM01. This transformant was cultured and treated in substantially the same manners as in Steps 1 and 2 of Example 1, thereby to obtain a crude extract containing mutanase. Using the crude extract, substantially the same procedures as in Steps 3 to 6 of Example 1 were repeated to obtain a highly purified mutanase product. The purity of the mutanase was determined in substantially the same manner as in Step 7 of Example 1, and it was found to be 99.5% or more. This showed that the allergens derived from the *Bacillus subtilis* were satisfactorily removed.

REFERENTIAL EXAMPLE 2

The antigen titer for the HBs antigen obtained in Step 6 of Example 1 was determined by radio-immunoassay as follows. The HBs antigen was subjected to serial doubling dilution with a 1/75M phosphate buffer saline containing 0.02 w/v % gelatin to prepare HBs antigen samples having respective dilutions. Using Auslia II kit manufactured and sold by Abott Co., U.S.A., each of the HBs antigen samples was separately reacted with the HBs antibodies adsorbed on beads at room temperature for 24 hours. Then, $^{125}$I-labeled HBs antibodies (Auslia II kit, manufactured and sold by Abott Co., U.S.A.) were added to each of the above-treated samples, and the mixtures obtained were maintained at 45° C. for 1 hour. Subsequently, with respect to the thus obtained beads which was linked with the HBs antigen which in turn was linked with the $^{125}$I-labeled HBs antibodies, the intensity of the radioactivity (cpm) was measured by means of a sintillation counter. From the intensity of the radioactivity (cpm), the antigen titer for the HBs antigen was calculated by the parallel line assay using the intensity of the radioactivity (cpm) of a control antigen. [See, for example, "Seibutsugakuteki Seizai Kijun Kaisetsu (Interpretation of Minimum Requirements for Biological Products)", pp. 435-448 (1973), Association of Biologicals Manufacturers of Japan] As a result, it was found that the antigen titer of the HBs antigen was 10.44 µg/ml, which showed that the HBs antigen obtained by the method of the present invention has an excellent antigenecity.

REFERENTIAL EXAMPLE 3

Using the HBs antigen as obtained in Step 6 of Example 1, a vaccine was prepared in accordance with the standard for adsorbed hepatitis B vaccine products as provided in Minimum Requirements for Biological Products (Notification No. 159 of the Ministry of Health and Welfare of Japan). That is, the HBs antigens were suspended in a physiological saline at a concentration of 40 µg/ml. Separately, aluminum hydroxide was suspended in a physiological saline at a concentration of 0.4 mg/ml. Then, equivolume of both the suspensions were mixed to prepare an aluminum hydroxide-adsorbed hepatitis B vaccine. The thus prepared vaccine satisfied all the requirements provided for by the above-mentioned standard.

The vaccine thus prepared was assayed for its titer using mice. That is, 1 ml of the vaccine was subcutaneously inoculated into each of ten BALB/c mice (5-week age) at the back. Five weeks after the inoculation, blood was collected from the ten mice, and the antibody titer for the blood was determined by passive hemagglutination.

Separately, a control assay was carried out using an "Adsorbed Hepatitis B Reference Vaccine" which was available for titer assays from the National Institute of Health, Tokyo, Japan. As a result, it was found that the relative titer of the vaccine prepared from the purified HBs antigen was 1.76 as against 1.0 for the control vaccine. This result indicates that the vaccine prepared from the HBs antigen purified by the method of the present invention has an excellent immunogenicity.

COMPARATIVE EXAMPLE 1

Substantially the same procedures as in Steps 1 to 6 of Example 1 were repeated except that one of the purification treatments was omitted as indicated in Table 2-1 to separately obtain HBs antigen products A to D. Using the thus obtained HBs antigen products A to D in place of the purified HBs antigen obtained in Step 6 of Example 1, PCA reaction test was conducted in substantially the same manner as in Step 8 of Example 1. The results are shown in Table 2-2. It is apparent from the results that the HBs antigen products A to D contained allergens remaining unremoved which are derived from the yeast cells.

TABLE 2-1

| Purification treatments | HBs antigen products | | | |
|---|---|---|---|---|
| | A | B | C | D |
| Adsorption treatment with silica gel | conducted | conducted | conducted | omitted |
| Adsorption treatment with active carbon | conducted | conducted | omitted | conducted |
| Density-gradient centrifugation | conducted once | conducted twice | conducted twice | conducted twice |
| Equilibrium density gradient centrifugation | conducted twice | conducted once | conducted twice | conducted twice |

TABLE 2-2

| HBs antigen products | Dose of HBs antigen product (μg protein) | PCA titer | IgE antibody |
|---|---|---|---|
| A | 8.0 | 10 | presence |
| | 4.0 | 5 | presence |
| | 2.0 | <5 | absence |
| | 1.0 | <5 | absence |
| | 0.5 | <5 | absence |
| B | 8.0 | 5 | presence |
| | 4.0 | <5 | absence |
| | 2.0 | <5 | absence |
| | 1.0 | <5 | absence |
| | 0.5 | <5 | absence |
| C | 8.0 | 10 | presence |
| | 4.0 | 5 | presence |
| | 2.0 | <5 | absence |
| | 1.0 | <5 | absence |
| | 0.5 | <5 | absence |
| D | 8.0 | 40 | presence |
| | 4.0 | 10 | presence |
| | 2.0 | 5 | presence |
| | 1.0 | <5 | absence |
| | 0.5 | <5 | absence |

What is claimed is:

1. A method for purifying a gene-expression product produced by recombinant DNA technique which consists essentially of the steps of:

(a) subjecting a crude aqueous solution containing a gene-expression product which solution is obtained from a culture of a transformant prepared by recombinant DNA technique to adsorption treatment with silica gel, thereby causing the gene-expression product to be adsorbed on said silica gel, (b) eluting said gene-expression product adsorbed on said silica gel to obtain an eluate containing the gene-expression product, (c) subjecting said eluate to adsorption treatment with active carbon, thereby causing impurities in said eluate to be adsorbed on said activated carbon, followed by recovery of the resulting eluate, (d) subjecting said resulting eluate treated in step (c) to density gradient centrifugation at least two times to obtain a preliminary fraction containing the gene-expression product, and (e) subjecting said preliminary fraction obtained in step (d) to equilibrium density gradient centrifugation at least two times to obtain a final fraction containing the gene-expression product;

said gene-expression product being free of allergens detectable by a passive cutaneous anaphylaxis reaction test.

2. The method according to claim 1, wherein the amount of said silica gel used in step (a) is in the range of from 0.1 to 10 w/v % based on said crude aqueous solution.

3. The method according to claim 1, wherein the amount of said activated carbon used in step (c) is in the range of from 0.1 to 10 w/v % based on said eluate.

4. The method according to claim 1, wherein at step (d)
the first density gradient centrifugation is effected using a centrifugal column which contains a carrier medium having a density gradient of a solute, said density gradient being such that the lowest solute concentration in said carrier medium is not lower than 5 w/w % and the highest solute concentration in said carrier medium is not higher than 60 w/w % and that the difference between said lowest and highest solute concentrations is from 10 to 55 w/w %, and
the second density gradient centrifugation and any subsequent density gradient centrifugation are effected using a centrifugal column which contains a carrier medium having a density gradient of a solute, said density gradient being such that the lowest solute concentration in said carrier medium is not lower than 5 w/w % and the highest solute concentration in said carrier medium is not higher than 50 w/w % and that the difference between said lowest and highest solute concentrations is from 5 to 45 w/w %.

5. The method according to claim 1, wherein at step (e)
the first equilibrium density gradient centrifugation is effected using a centrifugal column which contains a carrier medium having a solute concentration of from 10 to 40 w/w %, and
the second equilibrium density gradient centrifugation and any subsequent equilibrium density gradient centrifugation are effected using a centrifugal column which contains a carrier medium having a solute concentration of from 20 to 40 w/w %.

* * * * *